(12) United States Patent
Sohal et al.

(10) Patent No.: US 7,281,849 B2
(45) Date of Patent: Oct. 16, 2007

(54) SYSTEM AND METHOD FOR ALIGNMENT OF AN OBJECT IN A MEDICAL IMAGING DEVICE

(75) Inventors: Ratanjit Singh Sohal, Punjab (IN); Vikas Mohanrao Desai, Maharastra (IN)

(73) Assignee: General Electric Company, Schenectady, NY (US)

( * ) Notice: Subject to any disclaimer, the term of this patent is extended or adjusted under 35 U.S.C. 154(b) by 51 days.

(21) Appl. No.: 10/895,671

(22) Filed: Jul. 21, 2004

(65) Prior Publication Data

US 2006/0018438 A1 Jan. 26, 2006

(51) Int. Cl.
*A61B 6/08* (2006.01)
(52) U.S. Cl. ..................................... 378/206; 378/205
(58) Field of Classification Search ................ 378/205, 378/206, 63, 4–20; 356/152.3, 153, 141.1, 356/141.2, 399, 400

See application file for complete search history.

(56) References Cited

U.S. PATENT DOCUMENTS

| | | | |
|---|---|---|---|
| 4,117,337 A | 9/1978 | Staats | |
| 4,246,486 A * | 1/1981 | Madsen | 378/206 |
| 4,538,289 A * | 8/1985 | Scheibengraber | 378/20 |
| 4,836,671 A | 6/1989 | Bautista | |
| 5,095,386 A | 3/1992 | Scheibengraber | |
| 5,241,578 A | 8/1993 | MacMahon | |
| 5,661,775 A * | 8/1997 | Cramer et al. | 378/206 |
| 5,717,735 A | 2/1998 | Ramsdell et al. | |
| 5,727,042 A | 3/1998 | Brenneisen | |
| 5,823,192 A | 10/1998 | Kalend et al. | |
| 5,835,562 A | 11/1998 | Ramsdell et al. | |
| 5,982,546 A * | 11/1999 | Kawamoto et al. | 359/584 |
| 6,267,502 B1 | 7/2001 | McNeirney et al. | |
| 6,405,072 B1 | 6/2002 | Cosman | |
| 6,422,750 B1 * | 7/2002 | Kwasnick et al. | 378/205 |
| 6,516,046 B1 | 2/2003 | Frohlich et al. | |
| 6,662,036 B2 | 12/2003 | Cosman | |
| 6,739,751 B2 | 5/2004 | Williams | |
| 2002/0115928 A1 | 8/2002 | Hair | |

FOREIGN PATENT DOCUMENTS

WO WO 2004/034909 A1 4/2004

OTHER PUBLICATIONS

European Search Report, dated Nov. 17, 2005, App No/Pat No. 05254277.6—2305, reference No. 156282/10796, App No. EP 05 25 4277, date of completion of search Nov. 2, 2005, 3 pgs.

* cited by examiner

*Primary Examiner*—Jurie Yun
(74) *Attorney, Agent, or Firm*—Armstrong Teasdale LLP

(57) ABSTRACT

Systems and methods for alignment in a medical imaging device are provided. An alignment system includes a source of visible light and a reflector. The source of visible light is configured to project a beam of visible light within a field of view of the medical imaging device, and the reflector is configured to direct the projected beam of visible light along a central axis of the medical imaging device.

22 Claims, 7 Drawing Sheets

SYSTEM AND METHOD FOR ALIGNMENT OF AN OBJECT IN A MEDICAL IMAGING DEVICE

BACKGROUND OF THE INVENTION

This invention relates generally to medical imaging devices, and more particularly, to alignment systems in medical imaging devices, such as an X-ray imaging device, computed tomography (CT) imaging device and/or magnetic resonance imaging (MRI) device.

A medical imaging device typically includes an imager and a generator. A patient or an object under examination is placed between the imager and the generator to image. Positioners and aimers emitting visible light, for example a laser, help in aligning the patient's body with respect to the central axis of the medical imaging device. The alignment of the patient or the object under examination with the medical imaging device is important in order to reduce, for example, the number of iterations required to obtain an acceptable image and to reduce radiation dosage to which a patient is subjected.

Known lasers used in medical imaging devices for alignment of an object include imager side lasers and X-ray generator side lasers. These lasers also may be integrated lasers or detachable lasers. Further, different laser output shapes, such as, for example, a cross type laser and dot type laser may be provided.

In order to minimize the amount of radiation scatter on people around the medical imaging device during an imaging process, the imager is typically placed above a patient and the generator is placed below the patient. The laser is placed on the imager side because otherwise the laser beams from the generator side would fall on the table and not on the patient.

On the imager side, the laser cannot be placed in the field of view (FOV) because it may result in artifacts in the image. Therefore, the lasers are placed outside the imager edges. Moreover, in known designs, two lasers are used to generate a cross, which is then used to aim the X-ray radiation at the object under examination. Both the lasers emit beams that intersect to form a cross a certain distance from the imager. Because the FOV on the imager side is larger than that on the generator side, the lasers also have to be positioned a sufficient distance apart. This increases the distance at which the cross pattern is formed. In order to minimize the distance at which intersection of the laser beams occur, the span of the lasers is increased. However, increase in the span of the lasers increases leakage of the radiation beyond the generator, which is harmful, for example, to the people standing around the generator.

In generator-side laser systems, a late intersection may be acceptable, as the patient is not placed close to the radiation source. However, in the case of imager side lasers, late intersection is a disadvantage, as doctors often tend to keep patients closer to the imager rather than the generator.

In dot type laser systems, the dot tends to get lost when positioning, for example, a body. Therefore, it is more difficult to align the object with a dot than a cross pattern. In addition, in dot type lasers, a partial reflector is used within the FOV. The X-rays at the inlet of the imager are much weaker and hence even a small object near the imager creates a significant artifact, as compared to the artifact created by the same object when it is closer to the X-ray generator. Thus, imager side lasers are generally detachable type so that after the laser is used, it can be removed and artifacts reduced. This is an additional operation for the operator that adds time and complexity to the imaging process. Even in detachable type lasers, the dot lasers are often preferred as they provide a reference to the central axis throughout the free space as compared to cross-type lasers, which form the cross at a distance.

Therefore, known alignment systems for medical imaging devices are typically difficult to use and add time to the overall imaging process.

BRIEF DESCRIPTION OF THE INVENTION

In one embodiment of the invention, an alignment system for a medical imaging device is provided. The alignment system includes a source of visible light and a reflector, with the source of visible light configured to project a beam of visible light within a field of view of the medical imaging device and the reflector configured to direct the projected beam of visible light along a central axis of the medical imaging device.

In another embodiment of the invention, a method for providing an alignment reference within a medical imaging device is provided. The method includes projecting a single beam of visible radiation within a field of view of the medical imaging device. The method further includes directing the projected beam of visible radiation along a central axis of the medical imaging device.

DETAILED DESCRIPTION OF THE INVENTION

Various embodiments of the invention provide a system and a method for alignment of an object in a medical imaging device. The medical imaging device may be, for example, an X-ray imaging device, computed tomography (CT) imaging device and/or magnetic resonance imaging (MRI) device.

Figure 1:
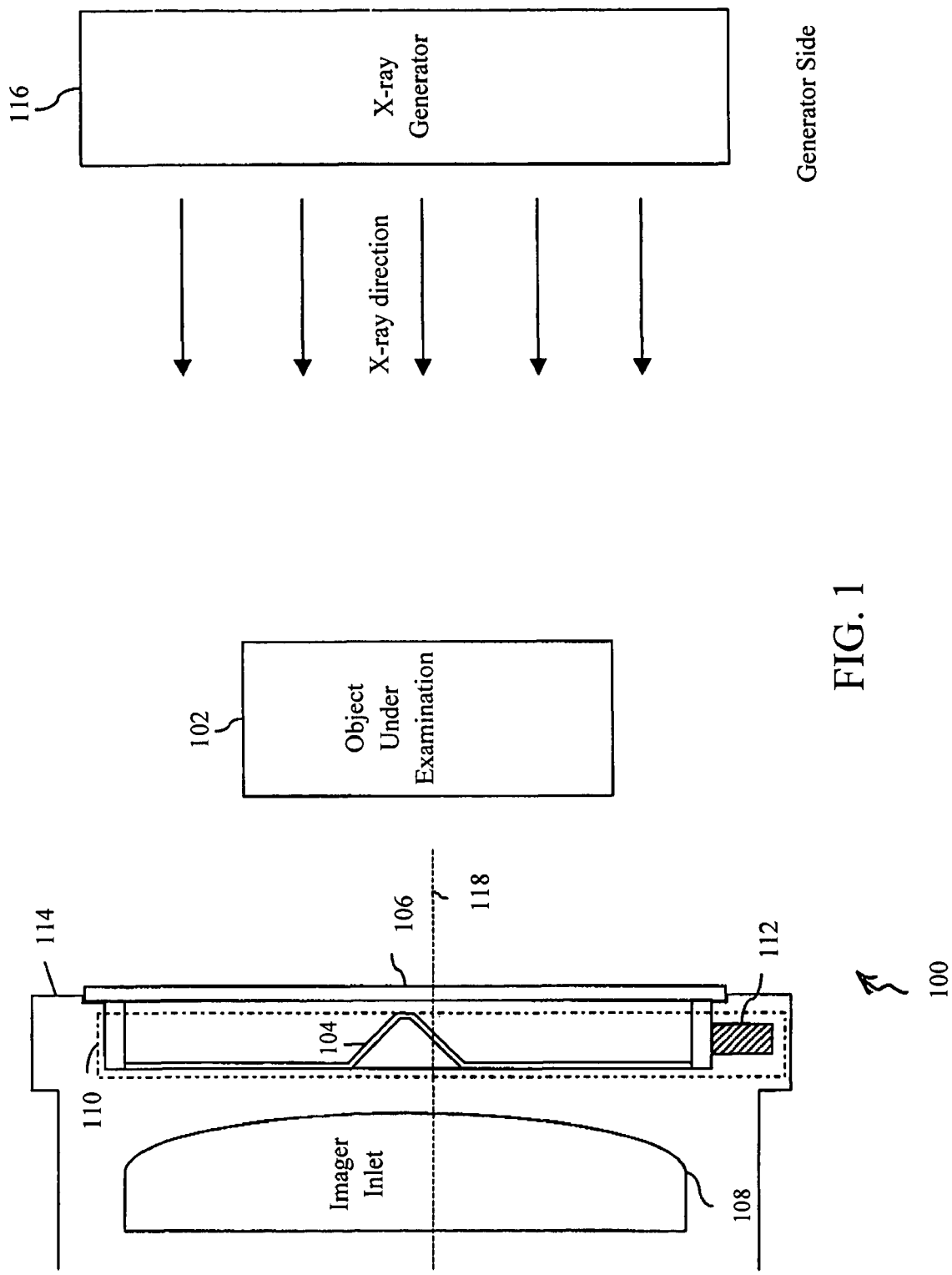
FIG. 1 is a block diagram illustrating a medical imaging device for X-ray imaging in accordance with an exemplary embodiment of the invention.

FIG. 1 illustrates a medical imaging device used for obtaining an image of an object in accordance with an exemplary embodiment of the invention. In one embodiment of the invention, the medical imaging device is an X-ray imaging device 100. X-ray imaging device 100 is used to examine an object 102. The medical imaging device includes a reflector 104, an X-ray grid 106, an imager inlet 108, an alignment system 110, a source of visible light (or radiation) 112, an imager 114 and an X-ray generator 116. In one embodiment of the invention, source of visible light 112 is a laser source and alignment system 110 is a laser-assisted alignment system. An X-ray generator side comprising X-ray generator 116 directs X-ray beam(s) on object 102 under examination. The X-ray beam, after passing through object 102 falls on imager 114. Imager 114 forms the image of object 102. The imager side includes imager 114 having X-ray grid 106, and an imager inlet 108. X-ray grid 106 is used to reduce and/or prevent scatter radiations from reaching imager 114. X-ray grid 106 may be constructed of different materials, for example, lead. A source of visible light 112 is mounted to the imager side, outside the field of view of the imager. Source of visible light 112 projects a laser beam within the FOV of the X-ray imaging device. A reflector 104 is mounted between X-ray grid 106 and imager inlet 108. Reflector 104 has at least one angled reflective surface. Alignment system 110, comprising source of visible light 112 and reflector 104, is used to project and direct a beam of visible light along a central axis 118 of X-ray imaging device 100.

Figure 2:
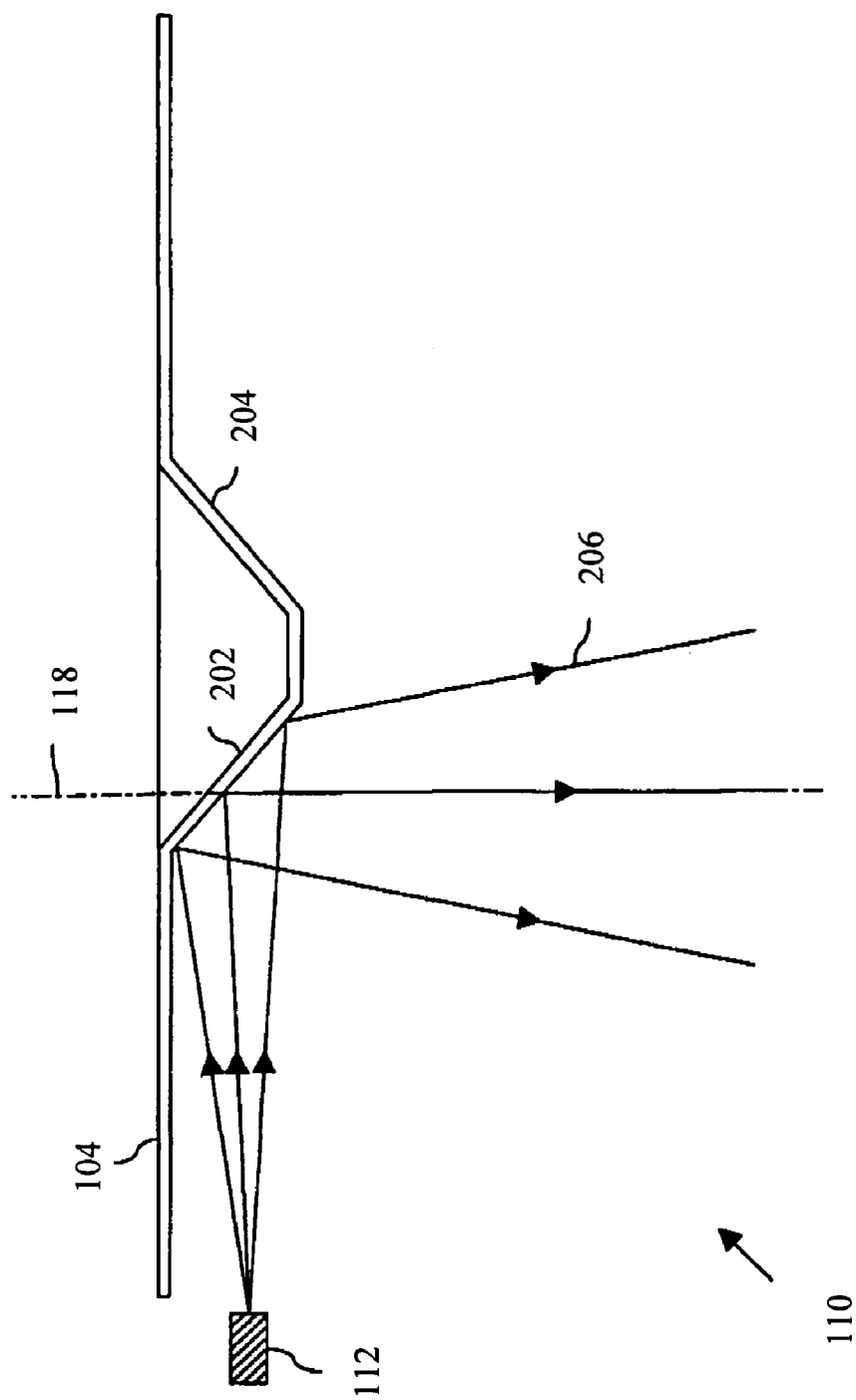
FIG. 2 is a block diagram illustrating an alignment system for a medical imaging device in accordance with an exemplary embodiment of the invention.
Figure 3:
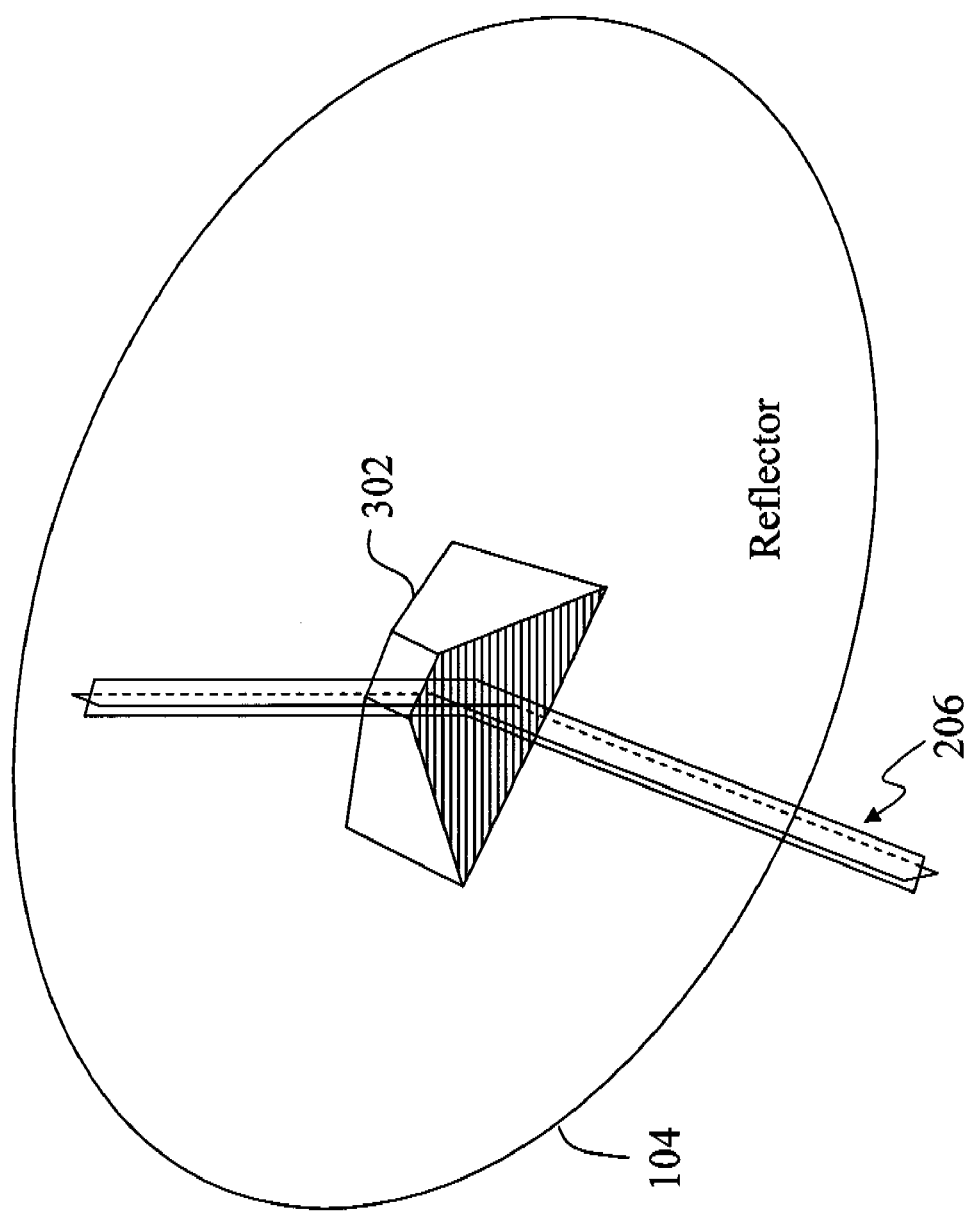
FIG. 3 is a diagram illustrating a reflector with at least one angled reflective surface in accordance with an exemplary embodiment of the invention.

FIG. 2 illustrates alignment system 110 for a medical imaging device in accordance with an exemplary embodiment of the invention. In one embodiment of the invention, the medical imaging device is an X-ray imaging device. Alignment system 110 includes source of visible radiation 112 and reflector 104. Source of visible light 112 is configured to project a beam 206 of visible light within the FOV of medical imaging device. Reflector 104 is configured to direct the projected beam 206 along central axis 118 of the medical imaging device. Source of visible light 112 is outside the FOV, for example, on side of, X-ray imaging device 100 and emits divergent cross beam 206. Beam 206 reflects on active reflecting surface 202 of reflector 104 and forms a symmetrical divergent cross pattern. Passive reflecting surface 204 is not functional in reflecting laser beam 206. FIG. 3 illustrates an exemplary cross beam 206 being reflected by reflector 104.

In one embodiment, source of visible radiation 112 in X-ray imaging device 100 includes a single laser having a double cylinder cross lens. Source of visible light 112 is configured to be positioned outside the FOV of the medical imaging device. Source of visible light 112 can be either removably connected to the medical imaging device or permanently connected to the medical imaging device.

FIG. 3 illustrates reflector 104 with at least one angled reflective surface in accordance with an exemplary embodiment of the invention. Reflector 104 in one embodiment includes a disc portion constructed of, for example, a thin polymer. Examples of polymers used for constructing the disc portion are polycarbonate, acrylic, polypropylene, glass and other such materials of low attenuation. Examples of the processes used for manufacturing the disc portion include vacuum forming, injection molding and thermal forming. The disc is of uniform thickness. The disc includes a projection 302 that is angled on one or more sides. The angle of inclination is configured such that a beam projected by the source of visible light 112 (shown in FIG. 2) is directed along central axis 118 (shown in FIG. 2) of the medical imaging device. In one embodiment of the invention, the surface of projection 302 is inclined at about 45° on all sides with the disc portion constructed of polycarbonate of a thickness about 0.5 mm. On the polycarbonate disc portion, a metal of thickness less than about 20 microns is deposited by, for example, Plasma Enhanced-Chemical Vapor Deposition (PE-CVD) or vapor deposition, to provide more than 90% specular reflectivity. Examples of metals that may be deposited on the polycarbonate disc include Aluminium, Gold, Silver, Mercury and Copper. In one embodiment, the aluminium coating is provided along the entire FOV. The aluminium coating may be covered with a protective layer that does not affect reflectivity. Exemplary materials used for a protective layer include, for example, polymerized layers, such as Plasil® and Glipoxan®. Plasil® is a polymerized layer of Protec™ available from Balzers Inc. Plasil® is made from the liquid monomer hexamethyldisiloxane (HMDSO).

In another embodiment of the invention, reflector 104 may be constructed of an aluminium plate with a reflective (e.g., shiny) surface that provides the same reflectivity as provided by Polycarbonate coated with aluminium.

Figure 4:
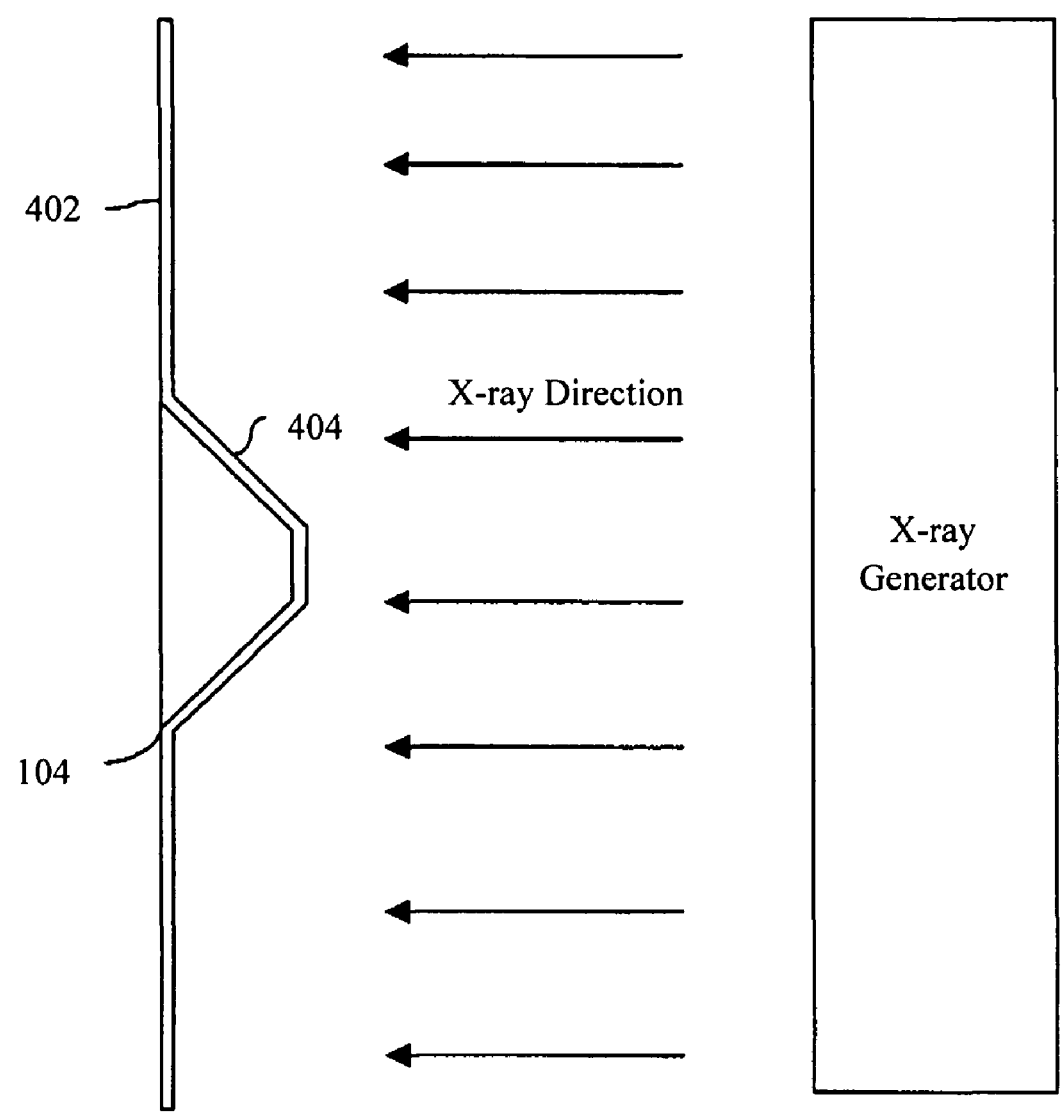
FIG. 4 is a block diagram illustrating the direction of X-ray with respect to the different surfaces of a reflector in accordance with an exemplary embodiment of the invention.

FIG. 4 illustrates the direction of X-ray with respect to the different surfaces of reflector 104 in accordance with an exemplary embodiment of the invention. The X-ray filtration provided by, for example, a 1 mm polycarbonate is equivalent to the X-ray filtration provided by 0.1 mm of aluminium. Therefore, a 0.5 mm thick polycarbonate disc portion provides a 0.05 mm aluminium equivalent filtration. Further, 10 microns of aluminium coating provided an added aluminium filtration of 0.01 mm. Therefore, the total aluminium equivalent filtration on the disc is 0.06 mm.

A planer surface 402 of reflector 104 in one embodiment is 0.06 mm thick. Therefore, as discussed above, it provides aluminium equivalent filtration equal to 0.06 mm. An inclined surface 404 of reflector 104 is also 0.06 mm thick. However, the filtration is maximum at inclined surface 404, because, at an inclination of 45 degrees, using Pythagoras theorem, the distance traveled by the X-ray in inclined surface 404 would be $(0.06^2+0.06^2)^{1/2}=0.0847$ mm. Hence, inclined surface 404 provides aluminium equivalent filtration of 0.0847 mm. Thus, the maximum difference in aluminium filtration that may occur with reflector 104 is 0.0847−0.06=0.0247 aluminium equivalent of filtration. This difference in filtration is not visually detectable during imaging.

In another embodiment of the invention, only active reflecting surface 202 of reflector 104 is metalized and there is no vapor deposition on passive reflecting surface 204.

Even in this case, the difference between the maximum and minimum aluminium equivalent filtration is 0.0347 mm aluminium equivalent.

Figure 5:
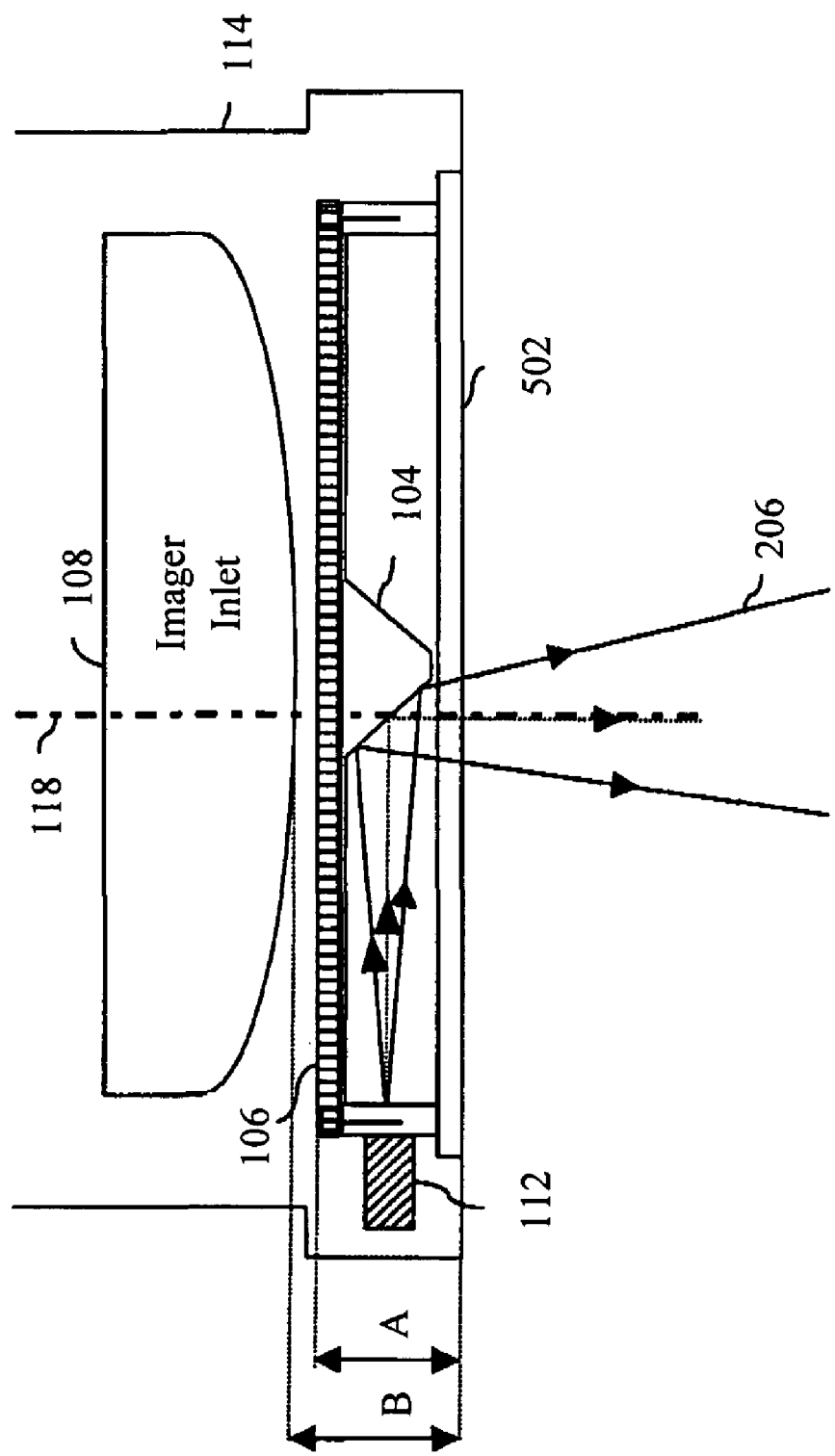
FIG. 5 is a cross sectional view of an imager of a medical imaging device in accordance with an exemplary embodiment of the invention.

FIG. 5 illustrates a cross sectional view of an imager of a medical imaging device in accordance with an exemplary embodiment of the invention. A filtering portion 502 (e.g., a filtering sheet) is used to filter the X-rays. Examples of the material used for filtering portion 502 include plane polycarbonate and red acrylic. In one embodiment of the invention, the thickness of filtering portion 502 is about 2 mm, resulting in filtration of 0.2 mm aluminium equivalent. In this embodiment of the invention, reflector 104 has an average aluminium equivalent filtration of 0.07 mm. Hence, the width of known grids 106 can be reduced by about 0.27 mm. The reduction in filtration because of the decrease in thickness of the grid is compensated by filtering portion 502 and reflector 104. In one embodiment of the invention, the cross section of source of visible light 112 is about 12 mm by 13 mm and the length of source of visible light 112 is about 25 mm.

Distance A is the gap between the outer surface of grid 106 and filtering portion 502. In one embodiment of the invention, A is about 24 mm. Distance B is the gap between the outer surface of filtering portion 502 and imager inlet 108. In some known X-ray imaging devices, B is about 26 mm.

Figure 6:
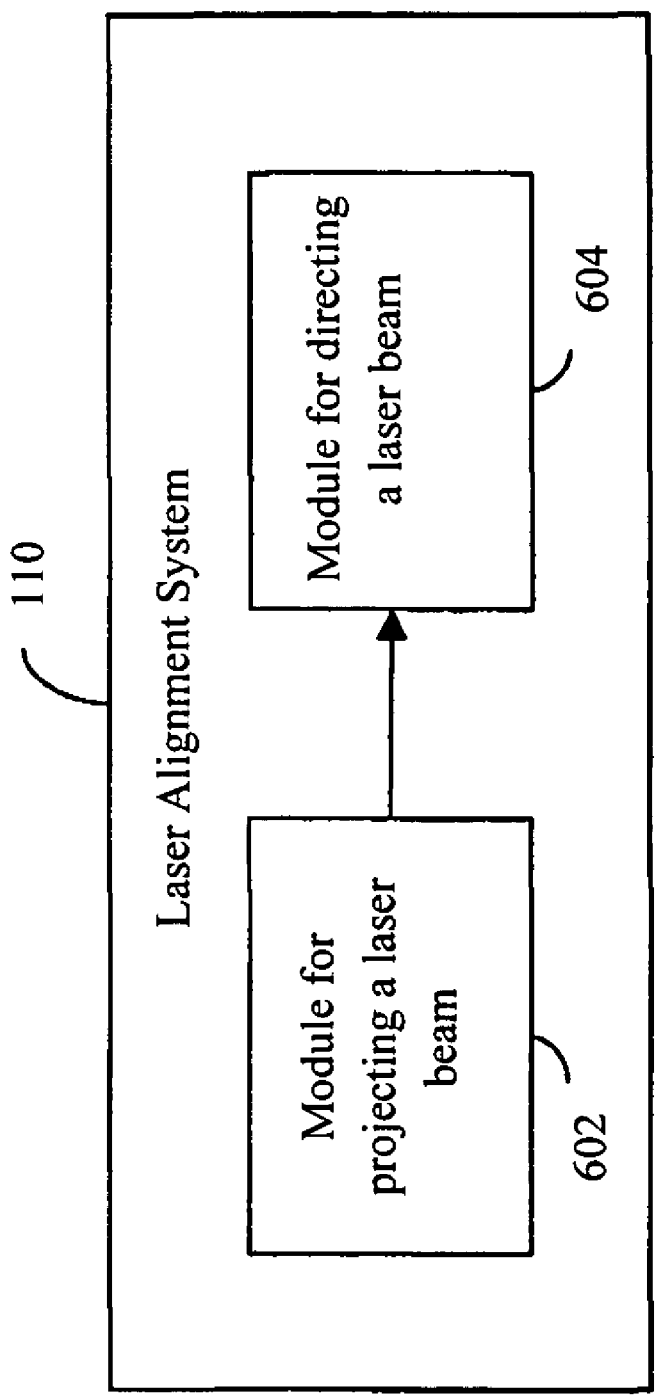
FIG. 6 is a block diagram illustrating an alignment system in accordance with an exemplary embodiment of the invention.

FIG. 6 is a block diagram illustrating alignment system 110. Alignment system 110 includes a means for projecting 602 and a means for directing 604. Means for projecting 602 projects a beam of visible radiation within the FOV of the medical imaging device as described herein. An exemplary means for projecting 602 is a source of visible light, for example, a laser, with a double cylinder cross lens. Means for directing 604 directs the projected beam of visible light along central axis 118 of the medical imaging device as described herein. An exemplary means of directing 604 is reflector 104 as described in conjunction with FIG. 1 and FIG. 3.

Figure 7:
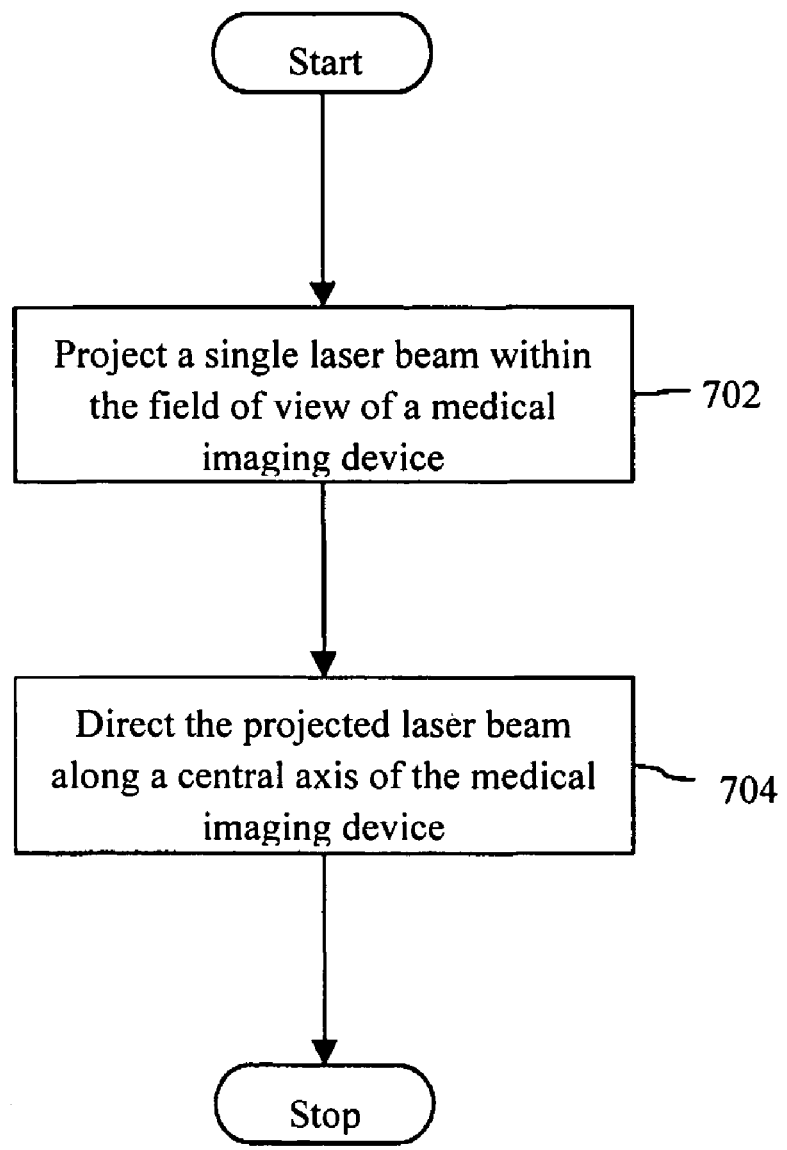
FIG. 7 is a flowchart illustrating a method for providing an alignment reference within a medical imaging device in accordance with an exemplary embodiment of the invention.

FIG. 7 is a flowchart illustrating a method for providing an alignment reference within a medical imaging device in accordance with an exemplary embodiment of the invention. A single laser beam is projected within the FOV of the medical imaging device at 702. The projected laser beam is then directed along a central axis of the medical imaging device using reflector 104 at 704. The cross reference-mark formed after directing the beam along the central axis is then used, for example, to position an object under examination.

The various embodiments of the invention provide both integrated and detachable imager side cross reference for alignment in a medical imaging device that have a non-discernable impact on image quality and provide cross type laser positioning and/or aiming reference throughout the central axis of the beam.

While the invention has been described in terms of various specific embodiments, those skilled in the art will recognize that the invention can be practiced with modification within the spirit and scope of the claims.

What is claimed is:

1. An alignment system for a medical imaging device, said alignment system comprising:

a source of visible light configured to project a cross-shaped beam of visible light within a field of view of a medical imaging device; and a reflector having a plurality of reflective surfaces and configured to direct the projected cross-shaped beam of visible light along a central axis that extends from an imager to a generator of the medical imaging device, the reflector being further configured to couple to the imager such that the reflector is positioned between the imager and the generator.

2. An alignment system in accordance with claim 1 wherein the source of visible light is a laser source.

3. An alignment system in accordance with claim 1 wherein the medical imaging device is an X-ray device and the source of visible light and reflector are configured to be positioned on an imager side of the X-ray device.

4. An alignment system in accordance with claim 1 wherein the medical imaging device is an X-ray device and wherein the source of visible fight is configured to be positioned outside a field of view of the X-ray device and the reflector is configured to be positioned between an X-ray grid and an imager inlet of the X-ray device.

5. An alignment system in accordance with claim 1 wherein the source of visible light is permanently coupled to the medical imaging device.

6. An alignment system in accordance with claim 1 wherein the source of visible light is configured to be removably coupled to the medical imaging device.

7. An alignment system in accordance with claim 1 wherein the source of visible light comprises a single laser.

8. An alignment system in accordance with claim 1 wherein the reflector comprises at least one angled reflective surface.

9. An alignment system in accordance with claim 1 wherein the reflector comprises a uniform thickness reflective surface.

10. An alignment system in accordance with claim 1 wherein the reflector comprises a vacuum metalized reflective surface.

11. An alignment system in accordance with claim 1 further comprising a metalized surface along the field of view of the medical imaging device adjacent the reflector.

12. An alignment system in accordance with claim 1 wherein the reflector comprises a polymer material provided by vacuum forming.

13. An alignment system in accordance with claim 1 wherein the source of visible light is configured to be positioned outside a field of view of the medical imaging device and perpendicular to the imaging direction.

14. An X-ray imaging device comprising:

an X-ray generator side including an X-ray generator;

an imager side including an imager having an X-ray grid and an imager inlet;

a source of visible radiation mounted to the imager side outside the field of view of the imager; and a reflector mounted within the field of view of the imager and between the X-ray grid and the imager inlet, the reflector having a plurality of angled reflective surfaces, wherein at least one of the angled reflective surfaces is configured to reflect a beam from the source of visible radiation along a central axis extending from the imager side to the X-ray generator side.

15. An X-ray imaging device in accordance with claim 14 wherein the source of visible radiation is a laser source.

16. An X-ray imaging device in accordance with claim 14 wherein the reflector is configured to direct a projected beam from the source of visible radiation along a central axis of the X-ray imaging device.

17. An X-ray imaging device in accordance with claim 14 wherein the source of visible radiation comprises a single laser.

18. An X-ray imaging device in accordance with claim 14 wherein the reflector comprises a full field polymer structure with a vacuum metalized portion forming the reflective surface.

19. An X-ray imaging device in accordance with claim 14 further comprising a reflective surface along a field of view surface of the imager.

20. An alignment system for a medical imaging device, said alignment system comprising:
    means for projecting a cross-shaped beam of visible radiation within a field of view of the medical imaging device; and
    a plurality of means for directing the projected cross-shaped beam of visible radiation along a central axis that extends from an imager to a generator of the medical imaging device, wherein said plurality of means are coupled to the imager such that said plurality of means are positioned between the imager and the generator.

21. A method for providing an alignment reference within a medical imaging device, said method comprising:
    projecting a single cross-shaped beam of visible radiation within a field of view of the medical imaging device;
    coupling a plurality of reflective surfaces to an imager such that the plurality of reflective surfaces are positioned between the imager and a generator; and
    directing the projected cross-shaped beam of visible radiation along a central axis extending from the imager to the generator using at least one of the plurality of reflective surfaces.

22. A method in accordance with claim 21 further comprising using an angled reflective surface to direct the projected cross-shaped beam of visible radiation.

* * * * *